United States Patent [19]

Boar et al.

[11] Patent Number: 5,585,378
[45] Date of Patent: Dec. 17, 1996

[54] COMPOSITION CONTAINING AN OXOINDOLE COMPOUND

[75] Inventors: Bernard R. Boar, Letchworth; Alan J. Cross, West Byfleet, both of Great Britain

[73] Assignee: Aktiebolaget Astra, Sodertalje, Sweden

[21] Appl. No.: 467,695

[22] Filed: Jun. 6, 1995

Related U.S. Application Data

[63] Continuation of Ser. No. 417,724, Apr. 6, 1995, abandoned, which is a continuation of Ser. No. 992,407, Dec. 17, 1992, abandoned.

[30] Foreign Application Priority Data

Dec. 18, 1991 [SE] Sweden .................. 9103752

[51] Int. Cl.$^6$ .................. A61K 31/495; A61K 31/445; C07D 403/06; C07D 401/06
[52] U.S. Cl. .................. 514/253; 514/323; 544/230; 544/373; 544/398; 544/364; 544/403; 546/201; 548/410; 548/485; 548/486
[58] Field of Search .................. 514/253; 544/373

[56] References Cited

U.S. PATENT DOCUMENTS

| | | | |
|---|---|---|---|
| 3,573,310 | 3/1971 | Van Dyke et al. | 544/373 |
| 3,810,896 | 5/1974 | Witte et al. | 544/376 |
| 4,060,526 | 11/1977 | Shetty | 544/393 |
| 4,382,934 | 5/1983 | Teraji et al. | 544/373 |
| 4,692,448 | 9/1987 | Devlin | 514/252 |
| 4,895,841 | 1/1990 | Sugimoto et al. | 514/212 |

FOREIGN PATENT DOCUMENTS

| 0010398 | 10/1979 | European Pat. Off. . |
|---|---|---|
| 9102725 | 8/1990 | WIPO . |

OTHER PUBLICATIONS

Kobayashi et al, *Chemical Abstracts*, vol. 109 No. 73323 (1988) (Abstract for JP 62 294654, Dec. 22, 1987).
Street et al, *J. Med. Chem.* 33 pp. 2690–2697 (1990).
W K Summers et al "Oral tetrahydroaminoacidine in long term treatment . . . " 1986 N.E. J. Medicine 315:1241.
C.A.98 (1983) Collino et al. "Mannich bases with benzimidazoles, benzotriazoles and . . . " 116650 w.
Collino et al Boll. Chim. Farm. 1982, 121, 221–29 R/N83991–57–5.

*Primary Examiner*—Emily Bernhardt
*Attorney, Agent, or Firm*—White & Case

[57] ABSTRACT

The present invention relates to an oxindole compound having the formula 5-cyclohexyl-1,3-dihydro-1-[2-[4-(phenylmethyl)-1-piperazinyl]ethyl]-2H-indol-2-one for the prevention or treatment of cognitive dysfunctions.

1 Claim, No Drawings

COMPOSITION CONTAINING AN OXOINDOLE COMPOUND

This application is a continuation of application Ser. No. 08/417,724, filed on Apr. 6, 1995, now abandoned which is a continuation of application Ser. No. 07/992,407, filed on Dec. 17, 1992, now abandoned.

FIELD OF THE INVENTION

The present invention relates to novel compounds having therapeutic activity, intermediates for their preparation, processes for their preparation, pharmaceutical formulations containing said compounds and medicinal use of said compounds and similar known compounds.

BACKGROUND OF THE INVENTION

A major characteristic of Alzheimer's Disease (Senile Dementia, SDAT) is a marked central cholinergic dysfunction. This cholinergic deficit has been reported to correlate with cognitive impairment (P. T. Francis et al, New Engl. J. Med., 1985, 313, 7). Various attempts to increase central cholinergic activity and thereby reverse the cognitive deficits have, to date, met with only limited success.

There is some evidence that use of the alkaloid physostigmine can, in some cases, be marginally beneficial, but the use of this compound in the clinic is compromised by a low therapeutic ratio, a short half-life and poor bioavailability. The cholinesterase inhibitor, 9-amino-1,2,3,4-tetrahydroacridine (THA) has been reported to be of therapeutic value in the treatment of a small group of patients with SDAT (W. K. Summers et al, New Engl. J. Med., 1986, 315, 1241). Further clinical trials of THA have produced some encouraging results but have been hampered by the association of this drug with certain toxic side effects.

Other compounds structurally related to either physostigmine or THA have been reported and are the subject of ongoing investigations.

There remains an urgent need for a safe and clinically effective drug for the symptomatic treatment of Alzheimer's Disease and related conditions.

A compound structurally similar to the compounds of the present invention, namely 1-[1-(4-benzyl-piperazinyl)methyl]isatin, is disclosed in Chemical Abstracts 98 (3):16650w referring to Boll Chim. Farm., 1992, 121 (5), pp. 221–9. Said compound is said to have pharmacological activity.

Japanese Patent Application No. 138443/86 (Publication No. KOKAI JP 62-294654A2) discloses 1-[2-(4-benzylpiperazinyl)ethyl]isatin as an intermediate for the synthesis of isatin derivatives which are useful as an agent for treating gastric or duodenal ulcer or mammals including human beings. Said single compound is deleted from the scope of the present invention by a disclosure in claim 1.

Furthermore, European Patent Application EP 0 010 398 relates to isatin derivatives useful for treating allergic symptoms. Among all specific compounds disclosed therein is only one falling within the general formula I of the compounds of the present invention, namely 1-[3-{4-(4-chlorobenzyl)-1-piperazinyl}propyl[-isatin. Said single compound is deleted from the scope of the present invention by a disclosure in claim 1 as well.

THE PRESENT INVENTION

A primary objective of the present invention is to provide structurally novel compounds which by virtue of their pharmacological profile enhance cholinergic function and are of value in the treatment of the cognitive dysfunctions which may be associated with ageing or with conditions such as Alzheimer's Disease, Senile and related Dementias, Parkinson's Disease, Down's Syndrome and Huntington's Chorea, and in the treatment of conditions such as glaucoma or myasthenia gravis. This utility is manifested, for example, by the ability of these compounds to inhibit the enzyme acetylcholinesterase. Further, the compounds of this invention are, in general, highly potent and selective, have an improved duration of action and are, in general, less toxic than hitherto known compounds.

The present invention relates to a compound having the general formula (1)

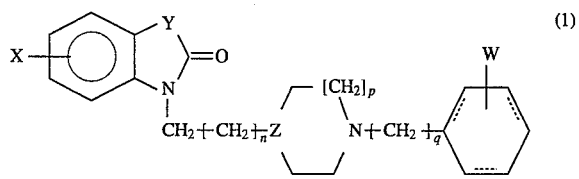

wherein:
n is 1, 2 or 3;
p is 1 or 2;
q is 1 or 2;
x represents one or more substituents independently selected from hydrogen, lower alkyl, aryl, aryloxy, CN, lower alkoxy, halogen, hydroxy, nitro, trifluoromethyl, alkylsulphonamido,
NHCOR where R is lower alkyl or aryl,
$NR_1R_2$ where $R_1$ and $R_2$ are independently hydrogen or lower alkyl or together form a ring,
$CO_2R$ where R is lower alkyl, or cycloalkyl, cycloalkenyl or bicycloalkyl either optionally further substituted by lower alkyl;
Y is CO or $CR_3R_4$ where $R_3$ and $R_4$ are independently hydrogen, lower alkyl, lower alkoxy or together form a cyclic acetal;
Z is N or CH;
and

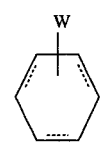

represents an optionally substituted phenyl or cyclohexyl group; wherein
W represents one or more substituents independently selected from hydrogen, lower alkyl, lower alkoxy or halogen;
stereo and optical isomers and racemates thereof where such isomers exist, as well as pharmaceutically acceptable acid addition salts thereof and solvates thereof;
with the provisos that the compound wherein n=1, p=1, q=1, X=H, Y=CO, Z=N and

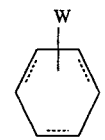

=unsubstituted phenyl and the compound wherein n=2, p=1, q=1, X=H, Y=CO, Z=N and

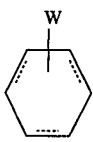

=4-chlorophenyl are excluded.

Preferred embodiments of this invention relate to compounds having the general formula (2)

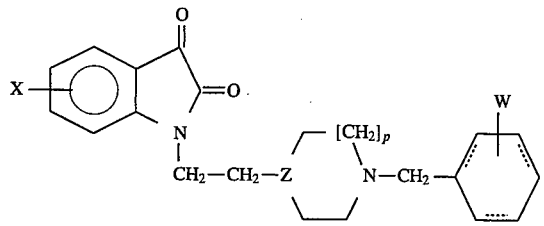

wherein p, X, W and Z are as previously defined above;
or to compounds having the general formula (3)

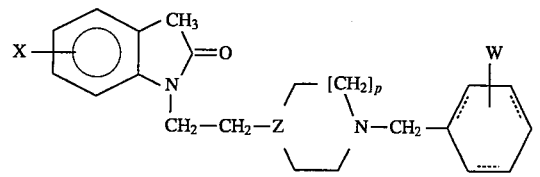

wherein p, X, W and Z are as previously defined above.

Throughout the specification and the appended claims, a given chemical formula or name shall encompass all stereo and optical isomers and racemates thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term "lower alkyl" denotes a straight or branched alkyl group having from 1 to 6 carbon atoms. Examples of said lower alkyl include methyl, ethyl, n-propyl, isopropyl, n-butyl, isobutyl, sec-butyl, t-butyl and straight- and branched-chain pentyl and hexyl.

Unless otherwise stated or indicated, the term "cycloalkyl" denotes a cyclic alkyl group having a ring size from $C_3$ to $C_7$, optionally additionally substituted by lower alkyl. Examples of said cycloalkyl include cyclopropyl, cyclobutyl, cyclopentyl, cyclohexyl, methylcyclohexyl and cycloheptyl.

Unless otherwise stated or indicated, the term "cycloalkenyl" denotes a cyclic alkenyl group having a ring size from $C_3$ to $C_7$, optionally additionally substituted by lower alkyl. Examples of said cycloalkenyl include cyclopropenyl, cyclobutenyl, cyclopentenyl, cyclohexenyl, methylcyclohexenyl and cycloheptenyl.

Unless otherwise stated or indicated, the term "aryloxy" denotes a phenoxy group in which the phenyl ring is optionally further substituted by lower alkyl, lower alkoxy or halogen.

Unless otherwise stated or indicated, the term "lower alkoxy" denotes a straight or branched alkoxy group having from 1 to 6 carbon atoms. Examples of said lower alkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term "halogen" shall mean fluorine, chlorine, bromine or iodine.

Unless otherwise stated or indicated, the term "aryl" denotes a phenyl, furyl or thienyl group in which the ring is optionally further substituted by lower alkyl, lower alkoxy or halogen.

Unless otherwise stated or indicated, the term "bicycloalkyl" denotes a bicyclic alkyl group having a size from $C_6$ to $C_9$, optionally additionally substituted by lower alkyl. Examples of said bicycloalkyl include bicyclo[2.2.1]heptyl, bicyclo[2.2.2]octyl and bicyclo[2.2.3]nonyl.

Unless otherwise stated or indicated, the term "cyclic acetal" denotes a cyclic acetal group having a ring size from $C_5$ to $C_7$. Examples of said cyclic acetal include 1,3-dioxolanyl and 1,3-dioxanyl.

Preferred compounds according to the invention are those of general formula (2) or general formula (3) in which:

p is 1,

W is hydrogen or F, especially 4-F,

X is lower alkyl, especially methyl or ethyl, lower alkoxy, especially methoxy or ethoxy, cycloalkyl, especially $C_5$ to $C_7$ cycloalkyl, F, aryl, especially phenyl, or $NR_1R_2$, especially 1-pyrrolidinyl or 1-piperidinyl. More preferred compounds according to the invention are those of general formula (2) or general formula (3) in which the X substituent is at the 5-position.

Among the most preferred compounds of formula (1) according to the present invention are 1,3-Dihydro-5-methyl-1-[2-[4-(phenylmethyl)-1-piperazinyl]ethyl]-2H-indol-2-one, 5-Cyclohexyl-1,3-dihydro-1-[2-[4-(phenylmethyl)-1-piperazinyl]ethyl]-2H-indol-2-one, 1,3-Dihydro-1-[2-[4-[(4fluorophenyl)methyl]-1-piperazinyl]ethyl]-5-methyl-2H-indol-2-one, 5-Cyclohexyl-1,3-dihydro-1-[2-[4-[4-fluorophenyl)methyl]-1-piperazinyl]ethyl]-2H-indol-2-one, 5-Methyl-1-[2-[4-(phenylmethyl)-1-piperazinyl]ethyl]-1H-indol-2,3-dione, 1-[2-[4-[(4-Fluorophenyl)methyl]-1 -piperazinyl]ethyl]-5-methyl-1H-indole-2,3-dione, 5-Cyclohexyl-1-[2-[4-(phenylmethyl)-1-piperazinyl]ethyl]-1H-indole-2,3-dione, 5-Fluoro-1-[2-[4-(phenylmethyl)-1-piperazinyl]ethyl]-1H-indole-2,3-dione, 1,3-Dihydro-5-fluoro-1-[2-[4-(phenylmethyl)-1-piperazinyl]ethyl]-2H-indol-2-one, 1,3-Dihydro-5-phenyl-1-[2-[4-(phenylmethyl)-1-piperazinyl]ethyl]-2H-indol-2-one, 1,3-Dihydro-1-[2-[4-(phenylmethyl)-1-piperazinyl]ethyl]-5-(1-piperidinyl)-2H-indol-2-one, 5-Cyclohexyl-1,3-dihydro-1-[2-[1-(phenylmethyl)-4-piperidinyl]ethyl]-2H-indol-2-one and pharmaceutically acceptable acid addition salts or solvates thereof.

The present invention also relates to processes for preparing the compound having formula (1). Said compound may be prepared by (a) reacting a compound of the general formula (4) or an acid addition salt thereof

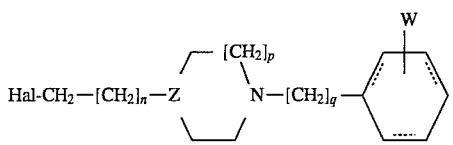

wherein Z, W, n, p and q are as defined above and Hal is halogen,
with a compound of the general formula (5)

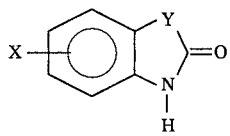

wherein X and Y are as defined above,
or, in the case where Z=N, by
(b) treating a compound of the general formula (5)

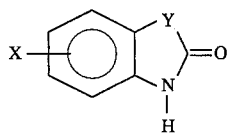

wherein X and Y are as defined above,
with a 1, (n+1)-dihaloalkane to obtain a compound of the general formula (6)

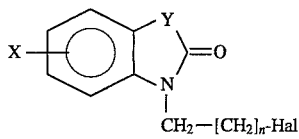

wherein X, Y and n are as defined above and Hal is halogen,
and reacting the compound of the general formula (6) with a compound of the general formula (7)

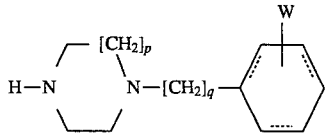

wherein W, p and q are as defined above.

The process (a) can be achieved, for example, by reacting together a compound of structure (4) or an acid addition salt thereof with a compound of structure (5) in a suitable solvent such as toluene or 3-methyl-2-butanone or dimethylsulphoxide or dimethylformamide in the presence of a base such as potassium hydroxide or triethylamine or anhydrous potassium carbonate, optionally with the addition of a catalytic amount of potassium iodide. Said reaction should be conducted at a suitable temperature, normally between 0° C. and 100° C., optionally in an inert atmosphere. In a preferred variation, a solution of the compound of structure (5) in dimethylformamide at 0° C. is treated with a strong base, preferably sodium hydride. After a suitable period of time the compound of structure (4) or an acid addition salt thereof is added to the reaction mixture and the process is then allowed to proceed at ambient temperature or above. The required product (1) may then be isolated and purified and characterised using standard techniques.

The process (b) can be achieved, for example, by treating a compound of structure (5) with a 1,ω-dihaloalkane, typically 1-bromo-2-chloroethane, in a suitable solvent such as toluene or 3-methyl-2-butanone or dimethylsulphoxide or dimethylformamide in the presence of a base such as triethylamine or anhydrous potassium carbonate. Such reaction should be conducted at a suitable temperature, normally between 0° C. and 100° C., optionally in an inert atmosphere. Some compounds of type (6) are known in the literature. The intermediate (6) may either be isolated and purified and characterised using standard techniques or else may be reacted in a crude form with a compound of structure (7). Such reaction is preferably conducted in a suitable solvent such as dimethylformamide in the presence of a base such as triethylamine or anhydrous potassium carbonate, optionally with the addition of a catalytic amount of potassium iodide. The reaction should be conducted at a suitable temperature, normally between 0° C. and 100° C., optionally in an inert atmosphere. The required product (1) may then be isolated and purified and characterised using standard techniques.

Compounds of structure (4) wherein Hal represents a halogen substituent, preferably either chloro or bromo, are, depending on the nature of the substituent W, either known compounds or compounds which can be prepared using known methods. The application of such methods to the synthesis of compounds of structure (4) will be readily understood by those skilled in the art.

Compounds of structure (5) wherein Y is CO are known as isatins (systematic name 1H-indole-2,3-diones). The isatins of structure (5) are, depending on the nature of the substituent(s) X, either compounds which have been previously described in the literature, or compounds which can be prepared by the straightforward application of known methods. The Sandmeyer procedure (Organic Syntheses, Coll. Vol. I., p 327), in which an aniline, chloral hydrate and hydroxylamine are reacted together to give an intermediate isonitrosoacetanilide which is then cyclised to the isatin on treatment with strong acid, is a particularly useful method.

Compounds of structure (5) in which Y is $CH_2$ are known as oxindoles (systematic name 1,3-dihydro-2H-indol-2-ones). The oxindoles of structure (5) are, depending on the nature of the substituent(s) X, either known compounds or compounds which can be prepared using known methods. The Gassman reaction (P. G. Gassman et al, J. Amer. Chem. Soc., 1974, 96, 5508 and 5512) constitutes a well-known and general synthesis of oxindoles.

Compounds of structure (5) wherein Y represents an acetal or cyclic acetal can be prepared from compounds of structure (5) wherein Y is CO by the straightforward application of known methods in a manner that will be readily understood by those skilled in the art.

Thus, the present invention also refers to some new intermediates of formulas (4) and (5), respectively, namely:

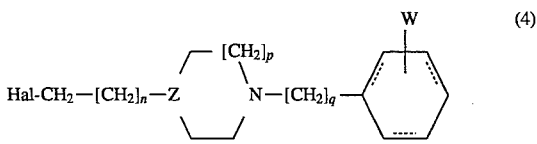

wherein Z and Hal are as defined above, n=p=q=1 and W=Me, OMe or F or

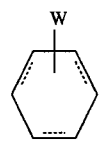

=cyclohexyl, with the proviso that the compound where Z=N and

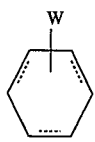

=2-methylphenyl is excluded, and

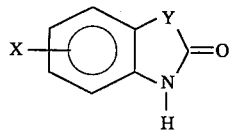 (5)

wherein

X is cycloalkyl, cycloalkenyl or bicycloalkyl, either optionally further substituted by lower alkyl or X is

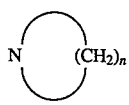

where n=4 to 7 and Y is $CH_2$ or CO or

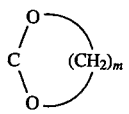

where m=2 to 4,
with the proviso that the compound where X=5-cyclohexyl and Y=CO is excluded.

In certain circumstances it is advantageous to prepare oxindoles from the corresponding isatins. This transformation may be achieved using such known methods as:

a) catalytic hydrogenation/hydrogenolysis;
b) formation of the corresponding 3-hydrazone followed by reductive elimination under basic conditions (Wolff-Kischner procedure); or
c) formation of the corresponding 3-dithioacetal followed by reduction using Raney nickel or nickel boride.

Method (c) represents a preferred process for the conversion of certain isatins (1;Y=CO) or (5;Y=CO) into the corresponding oxindoles (1;Y=$CH_2$) or (5;Y=$CH_2$) respectively.

The present invention also relates to pharmaceutical formulations containing a compound according to claim 1 as active ingredient and a pharmaceutically acceptable carrier.

Another object of the present invention is a compound according to claim 1 for use in therapy.

Still another object of the present invention is the use of a compound having the general formula (1)

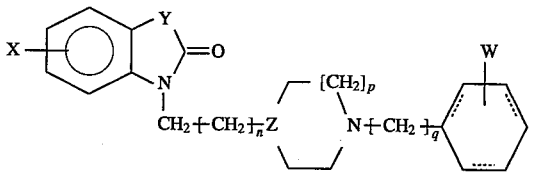 (1)

wherein:
n is 1, 2 or 3;
p is 1 or 2;
q is 1 or 2;

X represents one or more substituents independently selected from hydrogen, lower alkyl, aryl, aryloxy, CN, lower alkoxy, halogen, hydroxy, nitro, trifluoromethyl, alkylsulphonamido,
NHCOR where R is lower alkyl or aryl,
$NR_1R_2$ where $R_1$ and $R_2$ are independently hydrogen or lower alkyl or together form a ring,
$CO_2R$ where R is lower alkyl,
or cycloalkyl, cycloalkenyl or bicycloalkyl either optionally further substituted by lower alkyl;

Y is CO or $CR_3R_4$ where $R_3$ and $R_4$ are independently hydrogen, lower alkyl, lower alkoxy or together form a cyclic acetal;

Z is N or CH; and

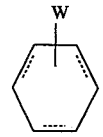

represents an optionally substituted phenyl or cyclohexyl group; wherein

W represents one or more substituents independently selected from hydrogen, lower alkyl, lower alkoxy or halogen;

stereo and optical isomers and racemates thereof where such isomers exist, as well as pharmaceutically acceptable acid addition salts thereof and solvates thereof, for the manufacture of a medicament for the treatment of conditions such as glaucoma and myasthenia gravis and more particularly, for the prevention or treatment of cognitive dysfunctions which may be associated with ageing or with conditions such as Alzheimer's Disease, Senile and related Dementias, Parkinson's Disease, Down's Syndrome and Huntington's Chorea.

Moreover, the present invention relates to a method for the treatment of cholinergic dysfunction whereby a pharmacologically effective amount of a compound according to claim 1 is administered to a host in need of said treatment.

Pharmacology

The compounds of general formula (1) of the present invention are useful in the treatment of various cognitive dysfunctions, such as those occurring in Alzheimer's disease. This utility is manifested by the ability of these compounds to inhibit the enzyme acetylcholinesterase.

Acetylcholinesterase Inhibition Assay

The ability of compounds in general to inhibit the acetylcholinesterase activity of rat brain homogenate was determined using the spectrophotometric method of Ellman et al, Biochem. Pharmacol., 1961, 7, 88. Results are expressed as $IC_{50}$ nanomolar (i.e. the nanomolar concentration of test compound required to inhibit enzyme activity by 50%).

Further the compounds of this invention potentiate cholinergic function in the brain such that when administered to rodents these compounds induce marked cholinergic effects such as tremor. These utilities are further demonstrated by the ability of these compounds to restore cholinergically deficient memory in a delayed non-matched to sample task.

Delayed Non-Matched to Sample Assay

Rats were trained on a delayed non-matched to sample task similar to that described by Murray et al, Psychopharmacology, 1991, 105, 134–136. Scopolamine, an anticholinergic that is known to cause memory impairment, induces an impairment in performance of this task. This impairment is reversed by compounds of the type described in the present invention.

Pharmaceutical formulations

The administration in the novel method of treatment of this invention may conveniently be oral, rectal, or parenteral at a dosage level of, for example, about 0.0001 to 10 mg/kg, preferably about 0.001 to 1.0 mg/kg and especially about 0.01 to 0.2 mg/kg and may be administered on a regimen of 1 to 4 doses or treatments per day. The dose will depend on the route of administration, a preferred route being by oral administration. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, syrups, powders or granules for oral administration; sterile parenteral administration; or as suppositories for rectal administration.

To produce pharmaceutical formulations containing a compound according to the present invention in the form of dosage units for oral application the active substance may be admixed with an adjuvant/a carrier e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the abovementioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.02% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in a aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

EXAMPLE 1

5-(1-Methylethyl)-1H-indole-2,3-dione 4-(1-Methylethyl)-aniline (6.75 g) was dissolved in water (30 ml) containing concentrated hydrochloric acid (4.4 ml). Hydroxylamine hydrochloride (16.9 g) in water (48 ml) and sodium sulphate decahydrate (100 g) in water (120 ml) were added, followed by chloral hydrate (16.5 g) in ethanol (180 ml). The reaction mixture was heated under reflux for 3 hours, then poured into water. The solid isonitroso-acetanilide intermediate was collected by filtration, washed and dried. This material was cooled in an ice-salt bath and concentrated sulphuric acid (48 ml) was added dropwise with stirring. After addition was complete the mixture was warmed to 80° C. for 20 minutes and then poured onto crushed ice. The resulting red solid was collected by filtration, washed, dried and then recrystallised from toluene-light petroleum to give the title compound, m.p. 127°–129° C.

$^m/z$ 207 (M+NH$_4^+$) and 190 (M+H$^+$).

$^1$H Nmr (CDCl$_3$) 1.16 (6H, d), 2.95 (1H, septuplet), 6.9 (1H, d), 7.45 (1H, dd), 7.5 (1H, d) and 9.0 (1H, br s).

EXAMPLE 2

5-Tetradecyl-1H-indole-2,3-dione

Following the method of Example 1 and starting from 4-tetradecylaniline, the title compound was obtained.

M.p. 87°–89° C.

$^m/z$ 361 (M+NH$_4^+$) and 344 (M+H$^+$).

EXAMPLE 3

5-Cyclohexyl-1,3-dihydro-2H-indol-2-one

5-Cyclohexyl-1H-indole-2,3-dione (3.4 g) in methanol (100 ml) was treated with 1,2-ethanedithiol (1.5 g) and boron trifluoride diethyletherate (2 ml). The mixture was stirred at room temperature overnight and then evaporated to dryness under reduced pressure. The residue was purified by flash chromatography to yield the corresponding dithioacetal. This material in ethanol (100 ml) was treated with Raney nickel (50% slurry in water, 40 g) and the mixture was heated under reflux overnight. The mixture was filtered through Celite and the residues washed thoroughly with ethanol. The combined filtrates were evaporated to give the title compound as a white solid (2.9 g, 88%), m.p. 153°–155° C.

$^1$H Nmr (d$_6$-DMSO) 1.2–1.5 (5H, m), 1.7–2.0 (5H, m), 2.5 (1H, m), 3.5 (2H, s), 6.8 (1H, d), 7.08 (1H, dd) and 7.15 (1H, d) ppm.

EXAMPLE 4

5-Ethyl-1,3-dihydro-2H-indol-2-one

The title compound was prepared from 5-ethyl-1H-indole-2,3-dione following the method of Example 3.

M.p. 136°–137° C.

$^1$H Nmr (CDCl$_3$) 1.25 (3H, t), 2.6 (2H, q), 3.55 (2H, s), 6.85 (1H, d), 7.05 (1H, dd), 7.1 (1H, d) and 8.9 (1H, br s) ppm.

EXAMPLE 5

1-(2-Chloroethyl)-4-[(2-methoxyphenyl)methyl]piperazine

2-Methoxybenzyl chloride (16 g) and 1-(2-hydroxyethyl)piperazine (13 g) in ethanol (50 ml) were heated under reflux for 4 hours. The solvent was removed under vacuum and the resulting oil was passed through a pad of silica gel eluting with 10% methanol-ammonia in dichloromethane to give 1-(2-hydroxyethyl)-4-[(2-methoxyphenyl)methyl]piperazine as a colourless oil (80%), $^{13}$C nmr (CDCl$_3$) 157.4, 130.3, 127.8, 125.2, 119.8, 110.0, 59.5, 57.6, 55.2, 54.8, 52.7 and 52.4 ppm. This material (15 g) was treated at 0° C. with thionyl chloride (15 ml). The mixture was then heated at reflux for 2 hours. Toluene was added and the mixture was evaporated under reduced pressure. The resulting solid was collected and washed thoroughly to give the dihydrochloride of the title compound as a white solid, m.p. 276°–279° C. (dec.).

Found: C, 48.1; H, 6.8; N, 8.0. $C_{14}H_{21}ClN_2O$. 2HCl. 0.5$H_2O$ requires C, 47.95; H, 6.9; N, 8.0%.

This solid was suspended in dichloromethane and extracted twice with 1N sodium hydroxide solution. The organic phase was then washed with water, dried, and evaporated to give 1-(2-chloroethyl)-4-[(2-methoxyphenyl)methyl]piperazine as an oil.

$^{13}C$ Nmr (CDCl$_3$) 157.6, 130.3, 127.9, 125.5, 120.0, 110.2, 59.6, 55.6, 55.1, 52.9, 52.6 and 40.7 ppm.

The following compounds of Examples 6 to 12 were prepared in an analogous manner to that of Example 5 starting from 1-(2-hydroxyethyl)piperazine and the appropriate chloride.

EXAMPLE 6

1-(2-Chloroethyl)-4-[(3-methoxyphenyl)methyl]piperazine $^{13}C$ Nmr (CDCl$_3$) 159.4, 139.5, 128.9, 121.2, 114.3, 112.2, 62.6, 59.6, 54.9, 52.9, 52.7 and 40.7 ppm.

Dihydrochloride, m.p. 282°–289° C. (dec.).

Found: C, 48.1; H 6.65; N, 7.9. $C_{14}H_{21}ClN_2O$. 2HCl. 0.5$H_2O$ requires C, 47.95; H, 6.9; N, 8.0%.

EXAMPLE 7

1-(2-Chloroethyl)-4-[(3-methylphenyl)methyl]piperazine $^{13}C$ Nmr (d$_6$-DMSO) 137.9, 137.0, 129.3, 128.0, 127.4, 125.7, 61.9, 59.1, 52.4, 52.4, 41.3 and 20.8 ppm.

Dihydrochloride—Found: C, 50.6; H, 7.1; N, 8.3. $C_{14}H_{21}ClN_2$. 2HCl. 0.5$H_2O$ requires C, 50.2; H, 7.2; N, 8.4%.

EXAMPLE 8

1-(2-Chloroethyl)-4-[(4-fluorophenyl)methyl]piperazine $^{13}C$ Nmr (d$_6$-DMSO) 162.9 and 159.34 (d, J 241 Hz), 134.20 and 134.15 (d, J 3.4 Hz), 130.46 and 130.34 (d, J 8.1 Hz), 114.81 and 114.50 (d, J 21 Hz), 61.0, 59.0, 52.4, 52.3 and 41.3 ppm.

Dihydrochloride, m.p. 253°–256° C. (dec.).

Found: C, 47.4; H, 59; N, 8.5; F, 5.8. $C_{13}H_{18}ClFN_2$. 2HCl requires C, 47.4; H, 6.1; N, 8.5; F, 5.8%.

EXAMPLE 9

1-(2-Chloroethyl)-4-(cyclohexylmethyl)piperazine $^{13}C$ Nmr (d$_6$-DMSO) 64.7, 59.1, 53.0, 52.5, 41.4, 34.3, 31.1, 26.3 and 25.4 ppm.

EXAMPLE 10

1-(2-Chloroethyl)-4-(2-phenylethyl)piperazine $^{13}C$ Nmr (CDCl$_3$) 140.1, 128.5, 128.2, 125.9, 60.3, 59.6, 53.0, 52.8, 40.7 and 33.4 ppm.

EXAMPLE 11

1-(2-Chloroethyl)-4-[(3-fluorophenyl)methyl]piperazine $^1$H Nmr (CDCl$_3$) 2.3–2.6 (8H, m), 2.7 (2H, t), 3.5 (2H, s), 3.55 (2H, t), 6.9 (1H, m), 7.1 (2H, m) and 7.2–7.3 (1H, m) ppm.

EXAMPLE 12

1-(2-Chloroethyl)-4-[(2-fluorophenyl)methyl]piperazine $^{13}C$ Nmr (CDCl$_3$) 162.3 and 158.7 (d), 130.6 (d), 128.8 (d), 123.9 (d), 123.0 (d), 114.5 and 114.2 (d), 64.0, 54.2, 52.3, 51.8 and 40.2 ppm.

Dihydrochloride—Found: C, 46.1; H, 6.2; N, 8.0. $C_{13}H_{18}ClFN_2$. 2HCl. 0.5$H_2O$ requires C, 46.1; H, 6.25; N, 8.3%.

EXAMPLE 13

5-Methyl-1-[2-[4-(phenylmethyl)-1-piperazinyl]ethyl]-1H-indole-2,3-dione Dihydrochloride 5-Methyl-1H-indole-2,3-dione (12.85 g) in dry DMF (50 ml) at 0° to 5° C. was treated with sodium hydride (80% dispersion in mineral oil, 2.53 g). The mixture was allowed to warm to room temperature and after a further 10 minutes 1-(2-chloroethyl)-4-(phenylmethyl)piperazine (20 g) in dry DMF (70 ml) was added. The mixture was heated at 70° C. for 3 hours and then evaporated under reduced pressure. The residue was subjected to flash chromatography on silica gel to afford the title compound (17.75 g). Treatment with ethanolic HCl then gave 5-methyl-1-[2-[4-(phenylmethyl)-1-piperazinyl]ethyl]-1H-indole-2,3-dione dihydrochloride (16.8 g), m.p. 270°–275° C. (dec.).

$^1$H Nmr (d$_6$-DMSO) 2.4 (3H,s), 3.3–3.9 (10H, m), 4.2 (2H, br s), 4.45 (2H, br s), 7.3 (1H, d), 7.45–7.6 (5H, m) and 7.75 (2H, m) ppm.

EXAMPLE 14

5-Cyclohexyl-1-[2-[4-(phenylmethyl)-1-piperazinyl]ethyl]-1H-indole-2,3-dione

5-Cyclohexyl-1H-indole-2,3-dione (3.45 g) in dry DMF at 0° C. was treated with sodium hydride (80% dispersion in mineral oil, 550 mg). The mixture was allowed to warm to room temperature and 1-(2-chloroethyl)-4-(phenylmethyl)piperazine (3.9 g) in dry DMF (25 ml) was added. The reaction mixture was then heated in an oil bath at 70° C. for 2 hours. The mixture was evaporated under reduced pressure and the residue passed through a pad of silica gel to yield the title compound as a red oil (4.2 g, 65%).

$^{13}C$ Nmr (CDCl$_3$) 183.8, 158.3, 148.9, 143.7, 137.9, 136.8, 129.0, 128.1, 126.9, 123.4, 117.6, 110.0, 62.8, 54.6, 53.1, 52.8, 43.6, 37.7, 34.2, 26.5 and 25.7 ppm. This oil (4 g) in ethanol (50 ml) was treated with ethanolic HCl to give 5-cyclohexyl-1-[2-[4-(phenylmethyl)-1-piperazinyl]ethyl]-1H-indole-2,3-dione dihydrochloride as an orange solid, m.p. 251°–254° C. (dec.).

The compounds of Examples 15 to 21 were prepared in an analogous manner to Examples 13 and 14, starting from 1-(2-chloroethyl)-4-(phenylmethyl)piperazine and the appropriately substituted 1H-indole-2,3-dione.

EXAMPLE 15

5-Butyl-1-[2-[4-(phenylmethyl)-1-piperazinyl]ethyl]-1H-indole-2,3-dione $^1$H Nmr (CDCl$_3$) 0.85 (3H, t), 1.25 (2H, m), 1.5 (2H, m), 2.4–2.9 (12H, m), 3.65 (2H, s), 3.75 (2H, t), 6.8 (1H, d) and 7.2–7.4 (7H, m) ppm.

Dihydrochloride, m.p. 217°–220° C. (dec.).

Found: C, 60.7; H, 7.0; N, 8.7. $C_{25}H_{31}N_3O_2$. 2HCl. $H_2O$ requires C, 60.5; H, 7.1; N, 8.5%.

EXAMPLE 16

5-(1-Methylethyl)-1-[2-[4-(phenylmethyl)-1-piperazinyl]ethyl]-1H-indole-2,3-dione $^m/z$ 391 (M$^+$), 189 and 91.

Dihydrochloride, m.p. 233°–234° C. (dec.).

Found: C, 58.7; H, 6.7; N, 8.6. $C_{24}H_{29}N_3O_2 \cdot 2HCl \cdot 1.5H_2O$ requires C, 58.7; N, 7.0; N, 8.55%.

EXAMPLE 17

5-Hexyl-1-[2-[4-(phenylmethyl)-1-piperazinyl]ethyl]-1H-indole-2,3-dione $m/z$ 433 (M$^+$), 189, 91.

Dihydrochloride, m.p. 223°–225° C. (dec.). $^1$H Nmr (d$_6$-DMSO) 0.9 (3H, t), 1.35 (6H, br s), 1.6 (2H, m), 2.6 (2H, t), 3.4–3.9 (10H, m), 4.15 (2H, br s), 4.45 (2H, br s), 7.25 (1H, d), 7.45 (1H, d), 7.5–7.6 (4H, m) and 7.7 (2H, m) ppm.

EXAMPLE 18

5-Ethyl-1-[2-[4-(phenylmethyl)-1-piperazinyl]ethyl]-1H-indole-2,3-dione.

$m/z$ 377 (M$^+$), 189, 91.

Dihydrochloride, m.p. 243°–245° C. (dec.).

Found: C, 60.9; H, 6.1; N, 9.2. $C_{23}H_{27}N_3O_2 \cdot 2HCl$ requires C, 61.3; H, 6.5; N, 9.3%.

EXAMPLE 19

1-[2-[4-(Phenylmethyl)-1-piperazinyl]ethyl]-5-tetradecyl-1-H-indole-2,3-dione

M.p. 67°–68° C.

$m/z$ 545 (M$^+$), 189, 91.

Found: C, 75.5; H, 9.65; N, 7.55. $C_{35}H_{51}N_3O_2 \cdot 0.5H_2O$ requires C, 75.8; H, 9.45; N, 7.6%.

EXAMPLE 20

5-(1-Methylpropyl)-1-[2-[4-(phenylmethyl)-1-piperazinyl]ethyl]-1H-indole-2,3-dione Dihydrochloride M.p. 235°–236° C. (dec.).

$^1$H Nmr (d$_6$-DMSO) 0.75 (3H, t), 1.15 (3H, d), 1.5 (2H, m), 2.6 (1H, m) 3.3–3.9 (10H, m), 4.1 (2H, br s), 4.4 (2H, br s), 7.25 (1H, d), 7.35–7.6 (5H, m) and 7.7 (2H, m) ppm.

Found: C, 62.5; H, 6.9; N, 8.55; Cl, 14.5. $C_{25}H_{31}N_3O_2 \cdot 2HCl$ requires C, 62.75; H, 6.95; N, 8.8; Cl, 14.8%.

EXAMPLE 21

5-(1,1-Dimethylethyl)-1-[2-[4-(phenylmethyl)-1-piperazinyl]ethyl]-1H-indole-2,3-dione Dihydrochloride M.p. 241°–242° C. (dec.).

$^1$H Nmr (d$_6$-DMSO) 1.3 (9H,s), 3.3–3.9 (10H, m), 4.1 (2H, br s), 4.35 (2H, br s), 7.25 (1H, d), 7.45 (3H, m), 7.55 (1H, d), 7.65 (2H, m) and 7.7 (1H, d) ppm.

EXAMPLE 22

1-[2-[4-(Cyclohexylmethyl)-1-piperazinyl]ethyl]-1H-indole-2,3-dione Dihydrochloride 1H-Indole-2,3-dione (2.4 g) in dry DMF (8 ml) at 0° C. was treated with sodium hydride (80% dispersion in mineral oil, 500 mg). The mixture was allowed to warm to room temperature and after 30 minutes 1-(2-chloroethyl)-4-(cyclohexylmethyl)piperazine (4 g) in dry DMF (8 ml) was added. The mixture was heated at 80° C. for 1.5 hours and then evaporated under reduced pressure. The residue was purified by flash chromatography on silica gel and then treated with ethanolic HCl to give 1-[2-[4-(cyclohexylmethyl)-1-piperazinyl]ethyl]-1H-indole-2,3-dione dihydrochloride, m.p. 256°–258° C.

Found: C, 57.9; H, 7.6; N, 9.5. $C_{21}H_{29}N_3O_2 \cdot 2HCl \cdot 0.5H_2O$ requires C, 57.7; H, 7.4; N, 9.6%.

By following the same procedure as in Example 22 but starting with the appropriate 4-substituted 1-(2-chloroethyl)piperazine the products of Examples 23 to 27 were obtained.

EXAMPLE 23

1-[2-[4-(2-Phenylethyl)-1-piperazinyl]ethyl]-1H-indole-2,3-dione Dihydrochloride M.p. 252°–254° C. (dec.).

Found: C, 59.7; H, 6.2; N, 9.2. $C_{22}H_{25}N_3O_2 \cdot 2HCl \cdot 0.5H_2O$ requires C, 59.3; H, 6.3; N, 9.4%.

EXAMPLE 24

1-[2-[4-[(2-Methoxyphenyl)methyl]-1-piperazinyl]ethyl]-1H-indole-2,3-dione Dihydrochloride M.p. 224°–225° C. (dec.).

$^1$H Nmr (d$_6$-DMSO) 3.4–4.0 (10H, m), 3.95 (3H, s), 4.25 (2H, br s), 4.4 (2H, br s), 7.1 (1H, t), 7.2 (2H, m), 7.4 (1H, d), 7.55 (1H, t), 7.65 (1H, d) and 7.75 (2H, m) ppm.

EXAMPLE 25

1-[2-[4-[(2-Methoxyphenyl)methyl]-1-piperazinyl]ethyl]-5-(1-methylethyl)-1H-indole-2,3-dione Dihydrochloride M.p. 215°–220° C. (dec.).

$m/z$ 422 (M+H$^+$).

Found: C, 59.9; H, 6.8; N, 8.4. $C_{25}H_{31}N_3O_3 \cdot 2HCl \cdot 0.5H_2O$ requires C, 59.6; H, 6.8; N, 8.35%.

EXAMPLE 26

1-[2-[4-[(3-Methoxyphenyl)methyl]-1-piperazinyl]ethyl]-1H-indole-2,3-dione Dihydrochloride M.p. 241°–244° C. (dec.).

$m/z$ 380 (M+H$^+$).

Found: C, 58.0; H, 6.0; N, 9.1. $C_{22}H_{25}N_3O_3 \cdot 2HCl$ requires C, 58.4; H, 6.0; N, 9.3%.

EXAMPLE 27

1-[2-[4-[(3-Methylphenyl)methyl]-1-piperazinyl]ethyl]-1H-indole-2,3-dione Dihydrochloride M.p. 242°–245° C. (dec.).

$m/z$ 364 (M+H$^+$)

$^1$H Nmr (d$_6$-DMSO) 2.4 (3H, s), 3.35–4.05 (10H, m), 4.25 (2H, br s), 4.45 (2H, br s), 7.25 (1H, t), 7.3–7.45 (3H, m), 7.55 (1H, d), 7.6 (1H, d), 7.65 (1H, d) and 7.75 (1H, t) ppm.

Found: C, 59.4; H, 6.2; N, 9.4. $C_{22}H_{25}N_3O_2 \cdot 2HCl \cdot 0.5H_2O$ requires C, 59.3; H, 6.3; N, 9.4%.

EXAMPLE 28

1-[2-[4-[(4-Fluorophenyl)methyl]-1-piperazinyl]ethyl]-1H-indole-2,3-dione

1H-Indole-2,3-dione (2.9 g) in dry DMF (5 ml) at 0° C. was treated with sodium hydride (80% dispersion in mineral oil, 600 mg). The mixture was warmed to 40° C. and after 45 minutes a solution of 1-(2-chloroethyl)-4-[(4-fluorophenyl)methyl]piperazine (5.1 g) in dry DMF (8 ml) was added. The reaction mixture was heated at 80° C. for 5 hours and then evaporated under reduced pressure. The residue was recrystallised twice to give 1-[2-[4-[(4-fluorophenyl)methyl]-1-piperazinyl]ethyl]-1H-indole-2,3-dione, m.p. 146°–147° C.

$^{13}$C Nmr (d$_6$-DMSO) 183.4, 162.9 and 159.3 (d), 157.9, 150.7, 138.1, 134.2 (d), 130.4 (d), 124.3, 123.0, 117.3, 114.8 and 114.5 (d), 110.9, 61.0, 54.2, 52.6, 52.4 and 37.2 ppm.

Found: C, 68.4; H, 6.3; N, 11.4. C$_{21}$H$_{22}$FN$_3$O$_2$ requires C, 68.65; H, 6.0; N, 11.4%.

Following the same general method as in Example 28 and using the appropriately substituted starting materials, the compounds of Examples 29 to 32 were prepared.

EXAMPLE 29

1-[2-[4-[(4-Chlorophenyl)methyl]-1-piperazinyl]ethyl]-1H-indole-2,3-dione

M.p. 126°–128° C. (dec.).

$^{13}$C Nmr (d$_6$-DMSO) 183.4, 157.9, 150.7, 138.1, 137.1, 131.3, 130.4, 128.0, 124.3, 123.0, 117.3, 110.9, 60.9, 54.1, 52.5, 52.4 and 37.2 ppm.

EXAMPLE 30

1-[2-[4-[(4-Fluorophenyl)methyl]-1-piperazinyl]ethyl]-5-methyl-1H-indole-2,3-dione $^{13}$C Nmr (CDCl$_3$) 183.7, 163.6 and 160.0 (d), 158.3, 148.7, 138.6, 133.6 (d), 133.3, 130.5 (d), 125.6, 117.6, 115.0 and 114.7 (d), 110.1, 62.0, 54.5, 53.1, 52.9, 37.7 and 20.5 ppm.

Dihydrochloride, m.p. 238°–240° C. (dec.).

Found: C, 57.1; H, 5.7; N, 9.2; C$_{22}$H$_{24}$FN$_3$O$_2$.2HCl. 0.5H$_2$O requires C, 57.0; H, 5.9; N, 9.1%.

EXAMPLE 31

1-[2-[4-[(2-Fluorophenyl)methyl]-1-piperazinyl]ethyl]-5-methyl-1H-indole-2,3-dione M.p. 104°–106° C.

$^1$H Nmr (CDCl$_3$) 2.25 (3H, s), 2.3–2.6 (10H, m), 3.5 (2H, s), 3.7 (2H, t), 6.75 (1H, d) and 6.9–7.4 (6H, m) ppm.

Dihydrochloride, m.p. 240°–246° C. (dec.).

Found: C, 57.3; H, 5.6; N, 8.9. C$_{22}$H$_{24}$FN$_3$O$_2$. 2HCl. 0.5 H$_2$O requires C, 57.0; H, 5.9%; N, 9.1%.

EXAMPLE 32

1-[2-[4-[(3-Fluorophenyl)methyl]-1-piperazinyl]ethyl]-5-methyl-1H-indole-2,3-dione $^{13}$C Nmr (CDCl$_3$) 183.7, 164.6 and 161.0 (d), 158.3, 148.7, 140.8 (d), 138.6, 133.3, 129.5 (d) 125.6, 124.5 (d), 117.6, 115.8 and 115.5 (d), 114.0 and 113.7 (d), 110.1, 62.2, 54.6, 53.1, 52.9, 37.8 and 20.6 ppm.

Dihydrochloride, m.p. 237°–240° C. (dec.).

EXAMPLE 33

4,7-Dimethyl-1-[2-[4-(phenylmethyl)-1-piperazinyl]ethyl]-1H-indole-2,3-dione Dihydrochloride 4,7-Dimethyl-1H-indole-2,3-dione (700 mg) in dry DMF (10 ml) was cooled to 0° C. and sodium hydride (80% dispersion in mineral oil, 120 mg) was added. After 30 minutes at 0° C. 1-(2-chloroethyl)-4-(phenylmethyl)piperazine (1 g) in dry DMF (5 ml) was added. The mixture was heated to 80° C. for 2 hours and then evaporated under reduced pressure. The residue was subjected to flash chromatography and then treated with ethanolic HCl to give 4,7-dimethyl-1-[2-[4-(phenylmethyl)-1-piperazinyl]ethyl]-1H-indole-2,3-dione dihydrochloride, m.p. 223°–227° C. (dec.).

$^m$/z 377 (M+H$^+$).

$^1$H Nmr (d$_6$-DMSO) 2.5 and 2.55 (each 3H, s), 3.3–4.0 (10H, m), 4.3 (2H, t), 4.45 (2H, br s), 6.9 and 7.4 (each 1H, d), 7.5 (3H, m) and 7.7 (2H, m) ppm.

Starting from the appropriately substituted 1H-indole-2,3-dione and following the method of Example 33 the compounds of Examples 34 to 42 were prepared.

EXAMPLE 34

4-Methyl-1-[2-[4-(phenylmethyl)-1-piperazinyl]ethyl]-1H-indole-2,3-dione Dihydrochloride M.p. 228°–230° C. (dec.).

$^m$/z 363 (M$^+$), 189 and 91.

Found: C, 59.0; H, 6.1; N, 9.5. C$_{22}$H$_{25}$N$_3$O$_2$. 2HCl. 0.5H$_2$O requires C, 59.3; H, 6.3; N, 9.4%.

EXAMPLE 35

5-Chloro-7-methyl-1-[2-[4-(phenylmethyl)-1-piperazinyl]ethyl]-1H-indole-2,3-dione $^{13}$C Nmr (d$_6$-DMSO) 199.3, 169.6, 150.6, 138.3, 135.4, 130.5, 129.8, 129.1, 128.3, 127.1, 120.9, 120.4, 62.3, 57.9, 52.8, 52.7, 44.0 and 20.0 ppm.

Dihydrochloride, m.p. 241°–243° C. (dec.).

$^m$/z 399 and 397 (M$^+$), 189 and 91.

EXAMPLE 36

5-Chloro-1-[2-[4-(phenylmethyl)-1-piperazinyl]ethyl]-1H-indole-2,3-dione Dihydrochloride M.p. 240°–243° C. (dec.).

EXAMPLE 37

5-Iodo-1-[2-[4-(phenylmethyl)-1-piperazinyl]ethyl]-1H-indole-2,3-dione Dihydrochloride M.p. 226°–229° C. (dec.).

$^1$H Nmr (d$_6$-DMSO) 3.3–4.0 (10H, m), 4.2 (2H, br s), 4.45 (2H, br s), 7.3 (1H, d), 7.5 (3H, m), 7.7 (2H, m), 7.9 (1H, d) and 8.05 (1H, dd) ppm.

EXAMPLE 38

4,7-Dichloro-1-[2-[4-(phenylmethyl)-1-piperazinyl]ethyl]-1H-indole-2,3-dione Dihydrochloride M.p. 248°–252° C. (dec.).

$^{13}$C Nmr (d$_6$-DMSO) 177.8, 158.6, 145.7, 139.5, 131.4, 130.3, 129.5, 129.1, 128.7, 125.7, 117.8, 114.2 and 35.4 ppm.

EXAMPLE 39

5-Nitro-1-[2-[4-(phenylmethyl)-1-piperazinyl]ethyl]-1H-indole-2,3-dione $^1$H Nmr (d$_6$-DMSO) 2.4–2.6 (8H, m), 2.7 (2H, t), 3.5 (2H, t), 3.55 (2H, s), 7.0 (1H, d), 7.3–7.5 (5H, m), 8.2 (1H, dd) and 8.6 (1H, d) ppm.

Dihydrochloride, m.p. 240°–245° C. (dec.).

EXAMPLE 40

5-Methoxy-1-[2-[4-(phenylmethyl)-1-piperazinyl]ethyl]-1H-indole-2,3-dione $^1$H Nmr (d$_6$-DMSO) 2.3 (4H, br s), 2.4–2.6 (6H, m), 3.4 (2H, s), 3.7–3.8 (5H, m), 7.15–7.2 (2H, m) and 7.25–7.4 (6H, m) ppm.

Dihydrochloride, m.p. 235°–245° C. (dec.).

Found: C, 58.1; H, 5.9; N, 9.1. C$_{22}$H$_{25}$N$_3$O$_3$. 2HCl requires C, 58.4; H, 6.0; N, 9.3%.

EXAMPLE 41

7-Methoxy-1-[2-[4-(phenylmethyl)-1-piperazinyl]ethyl]-1H-indole-2,3-dione Dihydrochloride M.p. 226°–229° C. (dec.).

EXAMPLE 42

1-[2-[4-(phenylmethyl)-1-piperazinyl]ethyl]-5-trifluoromethyl-1H-indole-2,3-dione $^1$H Nmr (CDCl$_3$) 2.3–2.6 (10H, m), 3.4 (2H, s), 3.8 (2H, t), 7.0 (1H, d), 7.25 (5H, br s) and 7.8 (2H, m) ppm.

Dihydrochloride, m.p. 235°–239° C. (dec.).

EXAMPLE 43

5-Methyl-1-[3-[4-(phenylmethyl)-1-piperazinyl]propyl]-1H-indole-2,3-dione

5-Methyl-1-indole-2,3-dione (1.54 g) in dry DMF (10 ml) at 0° C. was treated with sodium hydride (80% dispersion in mineral oil, 300 mg). The mixture was allowed to warm to room temperature and after a further 10 minutes 1-(3-chloropropyl)-4-(phenylmethyl)piperazine (2.53 g) in dry DMF (10 ml) was added. The mixture was heated at 80° C. for 3 hours and then evaporated under reduced pressure. The residue was purified by flash chromatography to give the title compound.

$^1$H Nmr (CDCl$_3$) 1.85 (2H, m), 2.3 (3H, s), 2.3–2.5 (10H, m), 3.5 (2H, s), 3.75 (2H, t), 6.9 (1H, d), and 7.2–7.4 (7H, m) ppm.

Treatment with ethanolic HCl gave 5-methyl-1-[2-[4-(phenylmethyl)-1-piperazinyl]propyl]-1H-indole-2,3-dione dihydrochloride m.p. 256°–261° C. (dec.).

EXAMPLE 44

1-[3-[4-(Phenylmethyl)-1-piperazinyl]propyl]-1H-indole-2,3-dione Dihydrochloride.

Following the method of Example 43 but starting with 1H-indole-2,3-dione, there was obtained the title compound. M.p. 233°–236° C. (dec.).

$^{13}$C Nmr (d$_6$-DMOS) 183.6, 158.8, 150.6, 138.7, 131.6, 130.0, 129.6, 129.3, 124.9, 123.8, 117.9, 111.0, 59.0, 53.3, 48.2, 47.6, 36.7 and 21.5 ppm.

EXAMPLE 45

5-Methyl-1-[4-[4-(phenylmethyl)-1-piperazinyl]butyl]-1H-indole-2,3-dione

5-Methyl-1H-indole-2,3-dione (1.6 g) in dry DMF (20 ml) at 0° C. was treated with sodium hydride (80% dispersion in mineral oil, 300 mg). After 30 minutes at 0° C., 4-bromo-1-chlorobutane (6.8 g) was added and the mixture was then heated at 90° C. for 2 hours. The mixture was evaporated to dryness under reduced pressure and the residue was treated with 1-benzylpiperazine (1.76 g) in dry DMF (20 ml). The resulting mixture was heated to 90° C. for 4 hours and then left to stand at room temperature overnight. The mixture was evaporated to dryness under reduced pressure and the residue was purified by flash chromatography to yield the title compound.

$^{13}$C Nmr (CDCl$_3$) 1.83, 158.2, 148.7, 138.7, 137.9, 133.5, 129.2, 128.2, 127.1, 125.8, 117.6, 110.1, 63.0, 57.6, 53.1, 53.0, 39.9, 25.0, 24.0 and 20.7 ppm.

Treatment with ethanolic HCl gave 5-methyl-1-[4-[4-(phenylmethyl)-1-piperazinyl]butyl]-1H-indole-2,3-dione dihydrochloride, m.p. 235°–238° C. (dec.).

EXAMPLE 46

1-[3-[4-(Phenylmethyl)-1-(hexahydro-1H-1,4-diazepinyl)] propyl]-1H-indole-2,3-dione Sodium hydride (80% dispersion in mineral oil, 140 mg) was added to a solution of 1H-indole-2,3-dione (660 mg) in dry DMF (6 ml) at 0° C. The mixture was allowed to warm to room temperature and after 30 minutes a solution of 1-(3-chloropropyl)-4-(phenylmethyl)-hexahydro-1H-1,4-diazepine (1.3 g) in dry DMF (8 ml) was added. The mixture was stirred at room temperature for 1 hour and then at 80° C. for 1 hour. The mixture was evaporated to dryness under reduced pressure and the residue was purified by flash chromatography to give the title compound as a red oil (820 mg, 48%).

$^1$H Nmr (d$_6$-DMSO) 1.6–1.7 (4H, m), 2.4–2.7 (10H, m), 3.5 (2H, s), 3.7 (2H, t) and 7.1–7.7 (9H, m) ppm.

EXAMPLE 47

5,6-Dimethoxy-1-[2-[4-(phenylmethyl)-1-piperazinyl] ethyl]-1H-indole-2,3-dione Dihydrochloride Anhydrous potassium carbonate (2.44 g) was added to a solution of 5,6-dimethoxy-1H-indole-2,3-dione (1.2 g) in dry DMF (5 ml). 2-Bromo-1-chloroethane (4.1 g) was added and the mixture was heated at 70° C. for 2 hours. The mixture was evaporated to dryness under reduced pressure and the residue was purified by flash chromatography on silica gel. The 1-(2-chloroethyl)-5,6-dimethoxy-1H-indole-2,3-dione thus obtained was dissolved in dry DMF (5 ml) and anhydrous potassium carbonate (2.44 g), potassium iodide (100 mg) and 1-(phenylmethyl)piperazine (3.06 g) were added. The mixture was stirred and heated at 70° C. for 2 hours and then evaporated to dryness under reduced pressure. The residue was purified by chromatography to yield a red oil which on treatment with ethanolic HCl afforded 5,6-dimethoxy-1-[2-[4-(phenylmethyl)-1-piperazinyl]ethyl]-1H-indole-2,3-dione dihydrochloride (33%), m.p. 205°–207° C. (dec.).

Following the general procedure of Example 47 but using the appropriately substituted 1H-indole-2,3-dione, the products of Examples 48 and 49 were prepared.

EXAMPLE 48

6-Methoxy-1-[2-[4-(phenylmethyl)-1-piperazinyl]ethyl]-1H-indole-2,3-dione

M.p. 136°–138° C.

EXAMPLE 49

7-Methyl-1-[2-[4-(phenylmethyl)-1-piperazinyl]ethyl]-1H-indole-2,3-dione $^{13}$C Nmr (d$_6$-DMSO) 200.6, 170.6, 151.9, 138.3, 136.5, 132.2, 129.2, 128.4, 127.2, 127.1, 120.1, 117.5, 62.3, 58.1, 52.7, 52.6, 44.2 and 20.3 ppm.

Dihydrochloride, m.p. 248°–249° C. (dec.).

EXAMPLE 50

1,3-Dihydro-1-[2-[4-(phenylmethyl)-1-piperazinyl]ethyl]-2H-indol-2-one

Sodium hydride (80% dispersion in mineral oil, 250 mg) was added to a solution of 1,3-dihydro-2H-indol-2-one (1.12 g) in dry DMF (5 ml at 0° C. The mixture was allowed to warm to room temperature and after 50 minutes a solution of 1-(2-chloroethyl)-4-(phenylmethyl)piperazine (2.02 g) in dry DMF (6 ml) was added. The reaction mixture was then heated at 80° C. for 2 hours and then evaporated to dryness under reduced pressure. The residue was purified by flash chromatography on silica gel to afford the title compound (1.1 g, 40%) as an oil.

$^{13}$C Nmr (d$_6$-DMSO) 174.1, 144.2, 138.1, 128.7, 128.0, 127.4, 126.7, 124.6, 124.1, 121.5, 108.3, 62.0, 54.6, 52.7, 52.5, 36.9 and 35.0.

Treatment with ethanolic HCl gave 1,3-dihydro-1-[2-[4-(phenylmethyl)-1-piperazinyl]ethyl]-2H-indol-2-one dihydrochloride, m.p. 253°–256° C. (dec.).

EXAMPLE 51

1,3-Dihydro-3,3-dimethyl-1-[2-[4-(phenylmethyl)-1-piperazinyl]ethyl]-2H-indol-2-one Dihydrochloride Following the general method of Example 50 but starting with 1,3-dihydro-3,3-dimethyl-2H-indol-2-one, there was obtained 1,3-dihydro-3,3-dimethyl-1-[2-[4-(phenylmethyl)-1-piperazinyl]ethyl]-2H-indol-2-one dihydrochloride, m.p. 218°–220° C. (dec.).

Found: C, 62.0; H, 7.4; N, 9.3. $C_{23}H_{29}N_3O$. 2HCl. 1.5 $H_2O$ requires C, 62.0; H, 7.2; N, 9.4%.

Starting with the appropriately substituted 1,3-dihydro-2H-indol-2-one and following the general method of Example 50 the compounds of Examples 52 to 54 were prepared.

EXAMPLE 52

1,3-Dihydro-7-methyl-1-[2-[4-(phenylmethyl)-1-piperazinyl]ethyl]-2H-indol-2-one Dihydrochloride M.p. 234°–236° C. (dec.).

$^m/z$ 349 ($M^+$), 189 and 91.

EXAMPLE 53

1,3-Dihydro-5-methyl-1-[2-[4-(phenylmethyl)-1-piperazinyl]ethyl]-2H-indol-2-one $^1H$ Nmr (CDCl$_3$) 2.3 (3H, s), 2.4–2.7 (10H, m), 3.4 (2H, s), 3.55 (2H, s), 3.75 (2H, t), 6.5 (1H, d), 7.0 (2H, m) and 7.2–7.35 (5H, m) ppm.

Dioxalate, m.p. 219°–223° C. (dec.).

Found: C, 57.3; H, 5.9; N, 7.5. $C_{22}H_{27}N_3O_2$. 2(CO$_2$H)$_2$. $H_2O$ requires C, 57.0; H, 6.1; N, 7.7%.

EXAMPLE 54

5-Cyclohexyl-1,3-dihydro-1-[2-[4-(phenylmethyl)-1-piperazinyl]ethyl]-2H-indol-2-one $^1H$ Nmr (CD$_2$Cl$_2$) 1.1–1.4 (5H, m), 1.6–1.8 (5H, m), 2.2–2.55 (11H, m), 3.3 (2H, s), 3.35 (2H, s), 3.65 (2H, t), 6.65 (1H, d), 6.95 (1H, dd), 7.0 (1H, d) and 7.1–7.25 (5H, m) ppm.

Dihydrochloride, m.p. 218°–220.5° C. (dec.).

Found: C, 64.1; H, 7.7; N, 8.0 $C_{27}H_{35}N_3O$. 2HCl. $H_2O$ requires C, 63.8; H, 7.7; N, 8.3%.

EXAMPLE 55

1,3-Dihydro-1-[3-[4-(phenylmethyl)-1-piperazinyl]propyl]-2H-indol-2-one Dioxalate Following the method of Example 43 but starting with 1,3-dihydro-2H-indol-2-one there was obtained the title compound. M.p. 216°–217° C.

Found: C, 56.9; H, 5.7; N, 7.5. $C_{22}H_{27}N_3O$. 2 $C_2H_2O_4$. $H_2O$ requires C, 57.0; H, 6.1; N, 7.7%.

Following one method of Example 50 but starting with the appropriately substituted 1,3-dihydro-2H-indol-2-one, the compounds of Examples 56 to 59 were prepared.

EXAMPLE 56

5-Cyclopentyl-1,3-dihydro-1-[2-[4-(phenylmethyl)-1-piperazinyl]ethyl]-2H-indol-2-one $^{13}C$ Nmr(CDCl$_3$) 174.6, 142.0, 140.1, 137.7, 128.8, 127.8, 126.7, 125.8, 124.3, 123.0, 107.6, 62.7, 54.6, 52.9, 52.6, 45.3, 37.3, 35.5, 34.4 and 25.2 ppm.

EXAMPLE 57

1,3-Dihydro-5-(1-methylpropyl)-1-[2-[4-(phenylmethyl)-1-piperazinyl]ethyl]-2H-indol-2-one $^{13}C$ Nmr(CDCl$_3$) 174.5, 142.0, 141.3, 137.5, 128.8 127.8, 126.7, 125.9 124.3, 122.8, 107.6, 62.5, 54.5, 52.8, 52.5, 41.0, 37.2, 35.4, 31.0, 21.9 and 12.0 ppm.

EXAMPLE 58

1,3-Dihydro-5-ethyl-1-[2-[4-(phenylmethyl)-1-piperazinyl]ethyl]-2H-indol-2-one $^{13}C$ Nmr(CDCl$_3$) 174.9, 142.1, 138.3, 137.5, 129.2, 128.2, 127.1, 126.8, 124.6, 124.1, 108.0, 62.8, 54.7, 53.0, 52.8, 37.5, 35.7, 28.4 and 16.0 ppm.

EXAMPLE 59

1,3-Dihydro-5-nitro-1-[2-[4-phenylmethyl)-1-piperazinyl]ethyl]-2H-indol-2-one

M.p. 134°–136° C.

$^{13}C$ Nmr(CDCl$_3$) 174.7, 150.3, 143.0, 137.6, 129.2, 128.2, 127.1, 125.1, 125.0, 120.2, 107.9, 62.8, 54.9, 53.2, 52.9, 38.1 and 35.2 ppm.

Dioxalate, m.p. 205°–208° C. (dec.)

Following the general method of Example 14 but starting with the appropriately substituted 1H-indole-2,3-dione the compounds of Examples 60 to 67 were prepared.

EXAMPLE 60

5-Cyclopentyl-1-[2-[4-(phenylmethyl)-1-piperazinyl]ethyl]-1H-indole-2,3-dione $^{13}C$ Nmr(CDCl$_3$) 189.9, 158.5, 148.9, 142.4, 137.9, 137.1, 129.2, 128.2, 127.1, 123.9, 117.7, 110.0, 63.0, 54.7, 53.2, 52.9, 45.1, 37.9, 34.5 and 25.3 ppm.

Dihydrochloride, m.p. 232°–240° C. (dec.).

$^m/z$ 418 (M+H$^+$).

EXAMPLE 61

7-Cyclopentyl-1-[2-[4-(phenylmethyl)-1-piperazinyl]ethyl]-1H-indole-2,3-dione $^{13}C$ Nmr (CDCl$_3$) 184.0, 160.6, 147.6, 138.0, 137.5, 131.6, 129.1, 128.1, 127.0, 124.1, 123.1, 119.8, 62.9, 55.2, 53.1, 53.0, 41.3, 39.0, 34.9 and 25.5 ppm.

EXAMPLE 62

5-Cycloheptyl-1-[2-[4-(phenylmethyl)-1-piperazinyl]ethyl]-1H-indole-2,3-dione $^{13}C$ Nmr(CDCl$_3$) 183.8, 158.4, 148.7, 145.7, 137.9, 136.6, 129.1, 128.1, 127.0, 123.4, 117.6, 110.0, 62.9, 54.6, 53.2, 52.9, 46.1, 37.8, 36.6, 27.7 and 26.9 ppm.

EXAMPLE 63

7-Cycloheptyl-1-[2-[4-(phenylmethyl)-1-piperazinyl]ethyl]-1H-indole-2,3-dione $^{13}C$ Nmr(CDCl$_3$) 184.0, 160.1, 145.8, 137.9, 137.8, 134.6, 129.2, 128.2, 127.0, 124.2, 123.1, 119.5, 63.0, 55.3, 53.2, 53.0, 41.1, 39.2, 36.6, 27.4 and 26.8 ppm.

EXAMPLE 64

5-Phenoxy-1-[2-[4-(phenylmethyl)-1-piperazinyl]ethyl]-1H-indole-2,3-dione Dihydrochloride M.p. 233°–236° C. (dec.)

$^m/z$ 442 (M+H$^+$)

Found: C, 61.8; H, 5.6; N, 8.0. $C_{27}H_{27}N_3O_3$. 2HCl. 0.5 $H_2O$ requires C, 61.95; H, 5.8; N, 8.0%.

EXAMPLE 65

5-Cyano-1-[2-[4-(phenylmethyl)-1-piperazinyl]ethyl]-1H-indole-2,3-dione Dihydrochloride
M.p. 244°–246° C. (dec.).
$m/z$ 375 (M+H$^+$).

EXAMPLE 66

5-Fluoro-1-[2-[4-(phenylmethyl)-1-piperazinyl]ethyl]-1H-indole-2,3-dione Dihydrochloride
$m/z$ 368 (M+H$^+$)
Found: C, 57.0; H, 5.6; N, 9.5. $C_{21}H_{22}N_3O_2F$. 2HCl requires C, 57.3; H, 5.5; N, 9.5%.

EXAMPLE 67

5-Ethoxy-1-[2-[4-(phenylmethyl)-1-piperazinyl]ethyl]-1H-indole-2,3-dione
$^{13}C$ Nmr(CDCl$_3$) 183.8, 158.2, 155.5, 144.6, 137.9, 129.0, 128.0, 126.8, 125.0, 117.8, 111.2, 109.9, 64.1, 62.8, 54.6, 52.9, 52.7, 37.7 and 14.5 ppm.

EXAMPLE 68

5-Amino-1,3-dihydro-1-[2-[4-(phenylmethyl)-1-piperazinyl]ethyl]-2H-indol-2-one
1,3-Dihydro-5-nitro-1-[2-[4-(phenylmethyl)-1-piperazinyl]ethyl]-2H-indol-2-one (200 mg) in ethanol (100 ml) containing 5% palladium on carbon (60 mg) was stirred under an atmosphere of hydrogen at STP for 1 hour. The catalyst was filtered off, the filtrate evaporated to dryness, and the residue purified by flash chromatography on silica gel.
$^{13}C$ Nmr(CDCl$_3$) 174.3, 141.8, 137.9, 136.4, 129.1, 128.1, 126.9, 125.8, 113.5, 112.7, 108.6, 62.9, 54.8, 53.1, 52.8, 37.5 and 35.9 ppm.
Trihydrochloride, m.p. 205°–220° C. (dec.).

EXAMPLE 69

5-Acetylamino-1,3-dihydro-1-[2-[4-(phenylmethyl)-1-piperazinyl]ethyl]-2H-indol-2-one
The compound of Example 68 and triethylamine in dry dichloromethane were treated with acetyl chloride. After 2 hours at RT the reaction was worked up and the product purified by flash chromatography on silica gel to afford the title compound, m.p. 145°–147° C.
$^{13}C$ Nmr (CDCl$_3$) 174.7, 168.5, 141.0, 137.9, 132.8, 129.2, 128.2, 127.0, 125.2, 119.9, 118.0, 108.2, 62.9, 54.8, 53.2, 52.9, 37.7, 35.9 and 24.3 ppm.
Following the general method of Example 50 but starting with the appropriately substituted 1,3-dihydro-2H-indol-2-one and using 1-(2-chloroethyl)-4-[(4-fluorophenyl)methyl] piperazine, the compounds of Examples 70 to 74 were obtained:

EXAMPLE 70

1,3-Dihydro-1-[2-[4-[(4-fluorophenyl)methyl]-1-piperazinyl]ethyl]-2H-indol-2-one Dioxalate
M.p. 202°–205° C. (dec.).
$m/z$ 354 (M+H$^+$).
Found: C, 55.5; H, 5.3; N, 7.8. $C_{21}H_{24}N_3OF$. 2 oxalate. 0.5H$_2$O requires C, 55.35; H, 5.4; N, 7.75%.

EXAMPLE 71

1,3-Dihydro-1-[2-[4-[(4-fluorophenyl)methyl]-1-piperazinyl]ethyl]-5-methyl-2H-indol-2-one Dioxalate
M.p. 206°–208° C. (dec.).
$m/z$ 368 (M+H$^+$).

Found: C, 55.6; H, 5.5; N, 7.1. $C_{22}H_{26}N_3OF$. 2 oxalate. H$_2$O requires C, 55.2; H, 5.7; N, 7.4%.

EXAMPLE 72

5-Cyclohexyl-1,3-dihydro-1-[2-[4-[(4-fluorophenyl)methyl]-1-piperazinyl]ethyl]-2H-indol-2-one
$^{13}C$ Nmr (CDCl$_3$) 174.6, 163.4 and 159.8 (doublet), 142.0, 133.4, 130.3, 130.2, 125.6, 124.3, 122.8, 114.8 and 114.5 (doublet), 107.7, 61.8, 54.6, 52.9, 52.5, 43.9, 37.2, 35.5, 34.4, 26.5 and 26.0 ppm.

EXAMPLE 73

1,3-Dihydro-5-fluoro-1-[2-[4-[(4-fluorophenyl)methyl]-1-piperazinyl]ethyl]-2H-indol-2-one Dihydrochloride
M.p. 227°–235° C. (dec.).
Found: C, 54.8; H, 5.7; N, 8.8. $C_{21}H_{23}F_2N_3O$. 2HCl. H$_2$O requires C, 54.6; H, 5.9; N, 9.1%

EXAMPLE 74

1,3-Dihydro-5-ethyl-1-[2-[4-[(4-fluorophenyl)methyl]-1-piperazinyl]ethyl]-2H-indol-2-one Dihydrochloride
M.p. 242°–243° C. (dec.).
Found: C, 58.4; H, 6.4; N, 8.6. $C_{23}H_{28}N_3OF$. 2HCl. H$_2$O requires C, 58.5; H, 6.8; N, 8.9%
Following the general method of Example 50 but starting with the appropriately substituted 1,3-dihydro-2H-indol-2-one, the compounds of Examples 75 to 88 were obtained.

EXAMPLE 75

1,3-Dihydro-5-fluoro-1-[2-[4-(phenylmethyl)-1-piperazinyl]ethyl]-2H-indol-2-one
$^{13}C$ Nmr (CDCl$_3$) 174.5, 160.8 and 157.0 (doublet), 140.5, 137.8, 129.2, 128.2, 127.0, 126.1 and 126.0 (doublet), 114.1 and 113.7 (doublet), 112.7 and 112.3 (doublet), 108.7 and 108.6 (doublet), 62.9, 54.8, 53.2, 52.9, 37.8 and 35.9 ppm.
Dihydrochloride, m.p. 214°–219° C. (dec.).

EXAMPLE 76

1,3-Dihydro-1-[2-[4-(phenylmethyl)-1-piperazinyl]ethyl]-5-trifluoromethyl-2H-indol-2-one
Dihydrochloride
M.p. 233°–237° C. (dec.).

EXAMPLE 77

1,3-Dihydro-7-fluoro-1-[2-[4-(phenylmethyl)-1-piperazinyl]ethyl]-2H-indol-2-one Dihydrochloride
M.p. 240°–247° C.
Found: C, 56.6; H, 6.3; N, 9.5. $C_{21}H_{24}FN_3O$. 2HCl. H$_2$O requires C, 56.8; H, 6.3; N, 9.5%.

EXAMPLE 78

5-Bromo-1,3-dihydro-1-[2-[4-(phenylmethyl)-1-piperazinyl]ethyl]-2H-indol-2-one Dihydrochloride
M.p. 260°–264° C. (dec.).

EXAMPLE 79

5-Cyano-1,3-dihydro-1-[2-[4-(phenylmethyl)-1-piperazinyl]ethyl]-2H-indol-2-one
$^{13}C$ Nmr (CDCl$_3$) 174.1, 148.3, 137.7, 132.9, 128.9, 127.9, 127.4, 126.8, 125.2, 119.0, 108.6, 104.8, 62.7, 54.7, 53.0, 52.7, 37.7 and 34.8 ppm.
Dihydrochloride, m.p. 247°–252° C. (dec.).

EXAMPLE 80

7-Cycloheptyl-1,3-dihydro-1-[2-[4-(phenylmethyl)-1-piperazinyl]ethyl]-2H-indol-2-one $^{13}$C Nmr (CDCl$_3$) 175.9, 139.6, 137.9, 132.4, 129.2, 128.1, 127.0, 126.9, 125.3, 122.4, 121.7, 63.0, 55.9, 53.3, 53.0, 40.4, 38.8, 37.2, 35.4, 27.5 and 27.2 ppm.

Dihydrochloride m.p. 210°–215° C. (dec.).

EXAMPLE 81

5-Cycloheptyl-1,3-dihydro-1-[2-[4-(phenylmethyl)-1-piperazinyl]ethyl]-2H-indol-2-one Dihydrochloride M.p. 212°–216° C. (dec).

EXAMPLE 82

5-Diethylamino-1,3-dihydro-1-[2-[4-(phenylmethyl)-1-piperazinyl]ethyl]-2H-indol-2-one $^{13}$C Nmr (CDCl$_3$) 174.5, 144.5, 137.9, 134.7, 129.2, 128.2, 127.0, 126.0, 111.9, 111.1, 108.8, 63.0, 54.9, 53.3, 53.0, 44.9, 37.6, 36.4 and 12.5 ppm.

Trihydrochloride, m.p. 188°–193° C. (dec.).

$m/z$ 406 (M$^+$), 189, 91.

EXAMPLE 83

1,3-Dihydro-1-[2-[4-(phenylmethyl)-1-piperazinyl]ethyl]-5-(1-pyrrolidinyl)-2H-indol-2-one $^{13}$C Nmr (CDCl$_3$) 174.3, 144.7, 137.9, 134.0, 129.2, 128.2, 127.0, 125.9, 109.8, 109.2, 108.8, 63.0, 54.9, 53.4, 52.9, 48.0, 37.6, 36.3 and 25.3 ppm.

Trihydrochloride, m.p. 233°–239° C.

$m/z$ 404 (M$^+$), 189, 91.

Found: C, 57.7; H, 7.3; N, 10.4. C$_{25}$H$_{32}$N$_4$O. 3HCl. 0.5 H$_2$O requires C, 57.4; H, 6.9; N, 10.7%.

EXAMPLE 84

1,3-Dihydro-1-[2-[4-(phenylmethyl)-1-piperazinyl]ethyl]-5-(1-piperidinyl)-2H-indol-2-one $^{13}$C Nmr (CDCl$_3$) 174.6, 148.7, 137.9, 137.5, 129.2, 128.1, 127.0, 125.4, 116.2, 115.4, 108.3, 62.9, 54.9, 53.2, 53.0, 52.2, 37.6, 36.1, 26.0 and 24.0 ppm.

EXAMPLE 85

1,3-Dihydro-5-ethoxycarbonyl-1-[2-[4-(phenylmethyl)-1-piperazinyl]ethyl]-2H-indol-2-one $^{13}$C Nmr (CDCl$_3$) 175.0, 166.2, 148.5, 137.8, 130.3, 129.0, 128.0, 126.9, 125.5, 124.3, 124.2, 107.7, 62.8, 60.6, 54.8, 53.1, 52.8, 37.8, 35.2 and 14.2 ppm.

EXAMPLE 86

1,3-Dihydro-5-methoxy-1-[2-[4-(phenylmethyl)-1-piperazinyl]ethyl]-2H-indol-2-one $^{13}$C Nmr (CDCl$_3$) 174.2, 155.3, 137.75, 137.7, 128.9, 127.9, 126.7, 125.6, 111.7, 111.6, 108.2, 62.7, 55.4, 54.6, 53.0, 52.7, 37.4 and 35.8 ppm.

EXAMPLE 87

1,3-Dihydro-6-methoxy-1-[2-[4-(phenylmethyl)-1-piperazinyl]ethyl]-2H-indol-2-one $^{13}$C Nmr (CDCl$_3$) 175.3, 159.7, 145.2, 137.6, 128.8, 128.0, 126.7, 124.5, 116.0, 105.5, 96.1, 62.6, 55.1, 54.6, 52.9, 52.5, 37.1 and 34.7 ppm.

EXAMPLE 88

1,3-Dihydro-4,5-dimethoxy-1-[2-[4-(phenylmethyl)-1-piperazinyl]ethyl]-2H-indol-2-one $^{13}$C Nmr (CDCl$_3$) 173.9, 147.6, 145.5, 138.3, 137.6, 128.7, 127.9, 126.7, 115.6, 111.2, 102.1, 62.6, 59.4, 55.9, 54.5, 53.0, 52.6, 37.4 and 33.8 ppm.

EXAMPLE 89

5-Benzoylamino-1,3-dihydro-1-[2-[4-(phenylmethyl)-1-piperazinyl]ethyl]-2H-indol-2-one The compound of Example 68 and triethylamine in dry dichloromethane were treated with benzoyl chloride. After 1 hour at RT the reaction was worked up and the product purified by flash chromatography on silica gel to afford the title compound.

$^{13}$C Nmr (CDCl$_3$) 174.8, 165.8, 141.1, 137.8, 134.7, 133.0, 131.8, 129.0, 128.5, 128.0, 127.1, 127.0, 125.1, 120.3, 118.2, 108.2, 62.9, 54.7, 53.1, 52.7, 37.7 and 35.8 ppm.

Dihydrochloride, m.p. 253°–256° C. (dec.).

EXAMPLE 90

1,3-Dihydro-5-methylsulphonamido-1-[2-[4-(phenylmethyl)-1-piperazinyl]ethyl]-2H-indol-2-one The compound of Example 68 in diethylether was treated with methanesulphonyl chloride. After 2 hours at RT the reaction was worked up and the product purified by flash chromatography on silica gel to yield the title compound.

M.p. 196°–198° C.

$m/z$ 428 (M$^+$), 189 and 91.

EXAMPLE 91

1,3-Dihydro-5-hydroxy-1-[2-[4-(phenylmethyl)-1-piperazinyl]ethyl]-2H-indol-2-one The compound of Example 86 in dry dichloromethane at −70° C. was treated under an atmosphere of dry nitrogen with boron tribromide (3.5 equivalents). The reaction mixture was allowed to warm to RT, stirred for 2 hours, and then evaporated under reduced pressure. The residue was stirred at RT with methanol for 1 hr and then worked up in the usual manner to give the title compound.

$^{13}$C Nmr (CDCl$_3$) 175.1, 152.5, 137.3, 136.2, 129.3, 128.2, 127.1, 125.8, 113.9, 112.9, 108.5, 62.8, 54.7, 52.9, 52.2, 36.9 and 36.1 ppm.

EXAMPLE 92

1,3-Dihydro-4,5-dihydroxy-1-[2-[4-(phenylmethyl)-1-piperazinyl]ethyl]-2H-indol-2-one The compound of Example 88 was treated by the general method of Example 91 to afford the title compound.

$^{13}$C Nmr (d$_6$-DMSO) 173.8, 142.1, 141.3, 137.7, 136.8, 128.8, 128.1, 126.9, 113.7, 110.5, 99.0, 61.8, 54.6, 52.5, 52.3, 36.9 and 33.4 ppm.

EXAMPLE 93

5'-Cyclohexyl-spiro[1,3-dioxolane-2,3'-[3H]-indol]-2'(1'H)-one

5-Cyclohexyl-1H-indole-2,3-dione (1 equivalent), ethane-1,2-diol (5 equivalents) and p-toluenesulphonic acid (0.02 equivalents) in dry toluene were heated under reflux overnight with azeotropic removal of water. The reaction mixture was cooled, washed with saturated sodium bicarbonate solution, and then worked up in the usual manner to afford the title compound.

M.p. 178°–180° C.

$^{13}$C Nmr (CDCl$_3$) 175.8, 143.4, 139.6, 129.9, 124.1, 123.4, 110.5, 102.6, 65.7, 44.1, 34.5, 26.8 and 26.0 ppm.

EXAMPLE 94

5'-Phenyl-spiro[1,3-dioxolane-2,3'-[3H]-indol]-2'(1'H)-one

5'-Bromo-spiro[1,3-dioxolane-2,3'-[3H]indol]-2'(1'H)-one (5.3 g) in dimethoxyethane (130 ml) and ethanol (33 ml) was treated with phenylboronic acid (7.2 g), tetrakis(triphenylphosphine)palladium (0) (0.5 g), triethylamine (4.1 ml) and 2M aqueous sodium carbonate (19.6 ml). The mixture was refluxed overnight, cooled, and filtered through a pad of silica gel. The filtrate was evaporated to dryness and the residue crystallised from ethyl acetate.

M.p. 189°–191° C.

$^m$/z 267.

$^{13}$C Nmr (d$_6$-DMSO) 174.4, 142.1, 139.5, 134.6, 129.8, 128.8, 127.0, 126.1, 125.5, 123.0, 110.8, 101.6 and 65.5 ppm.

EXAMPLE 95

5'-(Bicyclo[2.2.1]hept-2-yl)-spiro[1,3-dioxolane-2,3'-[3H]-indol]-2'(1'H)-one

5'-Iodo-spiro[1,3-dioxolane-2,3'-[3H]indol]-2'(1'H)-one (3.5 g), bicyclo[2.2.1]heptene (1.15 g), piperidine (3.2 g) and bis(triphenylphosphine)palladium (II) acetate (0.35 g) in DMF (5 ml) and formic acid (1.1 ml) were heated and stirred under nitrogen at 60° C. for 1 hour. The mixture was cooled, water (50 ml) and ethyl acetate (50 ml) were added, and after 5 minutes the organic layer was separated, washed, dried and evaporated to dryness. The residue was purified by flash chromatography to yield the title compound (60%).

M.p. 159°–161° C.

EXAMPLE 96

5'-Phenyl-1'-[2-[4-(phenylmethyl)-1-piperazinyl]ethyl]spiro[1,3-dioxolane-2,3'-[3H]indol]-2'(1'H)-one Following the general method of Example 14, 5'-phenyl-spiro[1,3-dioxolane-2,3'-[3H]indol]-2'(1'H)-one and 1-(2-chloroethyl)-4-(phenylmethyl)piperazine were reacted together to give the title compound. $^{13}$C Nmr (d$_6$-acetone) 173.9, 144.5, 141.0, 139.6, 136.6, 130.7, 129.7, 129.6, 128.9, 127.9, 127.6, 127.3, 126.2, 124.1, 110.6, 102.7, 66.5, 63.3, 55.6, 54.0, 53.8 and 38.0 ppm.

Dihydrochloride, m.p. 252°–254° C. (dec.).

EXAMPLE 97

5-Phenyl-1-1-[2-[4-(phenylmethyl)-1-piperazinyl]ethyl]-1H-indole-2,3-dione

The compound of Example 96 in a mixture of tetrahydrofuran (40 ml) and 3M hydrochloric acid (20 ml) was heated under reflux overnight. The mixture was cooled, basified by the addition of saturated aqueous sodium bicarbonate, and extracted with dichloromethane to yield the title compound.

$^{13}$C Nmr (d$_6$-acetone) 184.0, 158.5, 150.9, 139.5, 139.1, 136.7, 136.5, 129.3, 129.2, 128.4, 127.9, 127.1, 126.8, 122.8, 118.6, 111.8, 62.8, 55.0, 54.4, 53.3 and 38.0 ppm.

Dihydrochloride, m.p. 262°–265° C. (dec.).

EXAMPLE 98

5-(Bicyclo[2.2.1]hept-2-yl)-1-[2-[4-(phenylmethyl)-1-piperazinyl]ethyl]-1H-indole-2,3-dione Following the methods of Example 96 and 97, 5'-(bicyclo[2.2.1]hept-2-yl)-spiro[1,3-dioxolane-2,3'-[3H]indol]-2'(1'H)-one was converted into 5'-(bicyclo[2.2.1]hept-2-yl)-1'-[2-[4-phenylmethyl)-1-piperazinyl]ethyl]-spiro[1,3-dioxolane-2,3'-[3H]-indol]-2'(1'H)-one and thence into the title compound.

$^{13}$C Nmr (CDCl$_3$) 183.9, 158.4, 148.6, 143.4, 137.3, 137.0, 129.3, 128.2, 127.3, 123.5, 117.5, 110.0, 62.7, 54.5, 52.8, 52.7, 46.4, 42.7, 39.0, 37.7, 36.8, 35.9, 30.3 and 28.6 ppm.

Dihydrochloride, m.p. 242°–245° C. (dec.).

EXAMPLE 99

1,3-Dihydro-5-phenyl-1-[2-[4-(phenylmethyl)-1-piperazinyl]ethyl]-2H-indol-2-one

The compound of Example 97 (400 mg), ethane-1,2-dithiol (100 mg) and p-toluenesulphonic acid (500 mg) in glacial acetic acid (10 ml) were stirred at RT overnight. The mixture was evaporated to dryness. The residue was treated with aqueous sodium bicarbonate and extracted with dichloromethane. The extracts were washed, dried and evaporated to give 1,3-dihydro-3,3-ethylenedithio-5-phenyl-1-[2-[4-(phenylmethyl)-1-piperazinyl]ethyl]-2H-indol-2-one.

To this product (500 mg) in methanol (13 ml) and tetrahydrofuran (4 ml) was added nickel (II) chloride hexahydrate (1.6 g). The mixture was cooled to 0° C. and after 5 minutes, sodium borohydride (760 mg) was added. After a further 30 minutes at 0° C., the mixture was filtered through a pad of Celite. The filtrate was evaporated to dryness. The residue was dissolved in methanol (30 ml), 3M hydrochloric acid (20 ml) was added, and the mixture was heated under reflux for 2 hours. The methanol was removed under reduced pressure and the remaining aqueous solution was basified by the addition of saturated aqueous sodium bicarbonate. The mixture was extracted with dichloromethane. The material thus obtained was purified by flash chromatography to give the title compound.

$^{13}$C Nmr (d$_6$-acetone) 175.5, 145.7, 142.3, 140.1, 136.1, 130.2, 130.1, 129.4, 128.1, 128.0, 127.8, 127.5, 126.9, 124.4, 109.9, 63.9, 56.3, 54.6, 54.4, 38.7 and 36.4 ppm.

Dihydrochloride, m.p. 256°–258° C. (dec.).

EXAMPLE 100

5-(Bicyclo[2.2.1]hept-2-yl)-1,3-dihydro-1-[2-[4-(phenylmethyl)-1-piperazinyl]ethyl]-2H-indol-2-one Following the general method of Example 99, 5-(bicyclo[2.2.1]hept-2-yl)-1-[2-[4-(phenylmethyl)-1-piperazinyl]ethyl]-1H-indole-2,3-dione was converted into 5-(bicyclo[2.2.1]hept-2-yl)-1,3-dihydro-3,3-ethylenedithio-1-[2-[4-(phenylmethyl)-1-piperazinyl]ethyl]-2H-indol-2-one and thence into the title compound.

$^{13}$C Nmr (d$_6$-acetone) 174.8, 143.2, 141.7, 139.5, 129.6, 128.8, 127.5, 126.6, 125.5, 124.0, 108.6, 63.3, 55.8, 54.0, 53.8, 47.7, 44.0, 39.7, 38.0, 37.4, 36.4, 35.9, 31.0 and 29.3 ppm.

Dihydrochloride, m.p. 253°–254° C. (dec.).

EXAMPLE 101

5'-Methyl-1'-[2-[1-(phenylmethyl)-4-piperidinyl]ethyl]spiro[1,3-dioxolane-2,3'-[3H]-indol]-2'(1'H)-one 5'-Methyl-spiro[1,3-dioxolane-2,3'-[3H]indol]-2'(1'H)-one (1 equivalent) in dry DMF (5 ml) was added dropwise to sodium hydride (3 equivalents) in dry DMF (2 ml) at 0° C. After 20 minutes, a solution of 4-(2-chloroethyl)-1-(phenylmethyl)piperidine hydrochloride (1.5 equivalents) in dry DMF (15 ml) was slowly added. The mixture was heated to 80° C., stirred at this temperature for 3 hours, and then left at RT overnight. The mixture was evaporated to dryness under reduced pressure and the residue purified by flash chromatography to yield the title compound (53%).

13C Nmr (CDCl$_3$) 173.1, 141.5, 138.5, 132.8, 131.8, 129.2, 128.1, 126.9, 125.6, 124.0, 108.6, 102.1, 65.8, 63.4, 53.6, 37.5, 33.6, 33.4, 32.1 and 20.9 ppm.

EXAMPLE 102

5-Methyl-1-[2-[1-(phenylmethyl)-4-piperidinyl]ethyl]-1H-indole-2,3-dione

The compound of Example 101 (850 mg) in tetrahydrofuran (30 ml) was treated with 3M hydrochloric acid (17 ml). The mixture was heated under reflux overnight, then cooled, and neutralised by the addition of aqueous sodium bicarbonate. The mixture was extracted with dichloromethane. The extracts were washed, dried and evaporated and the residue was purified by flash chromatography to give the title compound.

13C Nmr (CDCl$_3$) 183.9, 158.1, 148.6, 138.7, 138.4, 133.5, 129.2, 128.1, 126.9, 125.8, 117.6, 109.9, 63.4, 53.6, 37.9, 33.7, 33.3, 32.1 and 20.7 ppm.

Hydrochloride, m.p. 195°–197° C.

Following the general methods of Examples 101 and 102 and starting from the appropriately substituted spiro [1,3-dioxolane-2,3'-[3H]indol]-2'(1'H)-one, the compounds of Examples 103 and 104 were prepared.

EXAMPLE 103

5-Methoxy-1-[2-[1-(phenylmethyl)-4-piperidinyl]ethyl]-1H-indole-2,3-dione

13C Nmr (CDCl$_3$) 183.7, 158.0, 156.3, 144.5, 138.3, 129.0, 128.0, 126.8, 124.4, 117.9, 110.9, 109.6, 63.2, 55.8, 53.4, 37.8, 33.5, 33.2 and 32.0 ppm.

EXAMPLE 104

5-Cyclohexyl-1-[2-[1-(phenylmethyl)-4-piperidinyl]ethyl]-1H-indole-2,3-dione

13C Nmr (CDCl$_3$) 183.8, 158.3, 148.7, 143.9, 136.8, 129.5, 128.2, 127.4, 123.6, 117.7, 109.8, 62.9, 53.2, 43.7, 37.8, 34.2, 33.5, 33.0, 31.4, 26.6 and 25.8 ppm.

Hydrochloride, m.p. 211°–213° C.

EXAMPLE 105

1,3-Dihydro-5-methyl-1-[2-[1-(phenylmethyl)-4-piperidinyl]ethyl]-2H-indol-2-one

The compound of Example 102 was reacted according to the general method of Example 99 to give the title compound.

13C Nmr (CDCl$_3$) 174.6, 142.0, 138.3, 131.4, 129.1, 128.3, 127.9, 126.7, 125.2, 124.6, 107.8, 63.2, 53.5, 37.6, 35.6, 33.7, 33.5, 31.9 and 20.9 ppm.

EXAMPLE 106

1,3-Dihydro-5-methoxy-1-[2-[1-(phenylmethyl)-4-piperidinyl]ethyl]-2H-indol-2-one The compound of Example 103 was reacted according to the general method of Example 99 to give the title compound.

13C Nmr(CDCl$_3$) 174.2, 155.5, 138.2, 137.8, 129.0, 128.0, 126.7, 125.9, 112.0, 111.8, 108.2, 63.2, 55.6, 53.4, 37.6, 35.9, 33.7, 33.3 and 32.0 ppm.

EXAMPLE 107

5-Cyclohexyl-1,3-dihydro-1-[2-[1-(phenylmethyl)-4-piperidinyl]ethyl]-2H-indol-2-one The compound of Example 104 was reacted according to the general method of Example 99 to give the title compound.

13C Nmr(CDCl$_3$) 174.8, 142.4, 142.3, 138.4, 129.1, 128.1, 126.8, 125.8, 124.7, 123.1, 107.9, 63.4, 53.6, 44.2, 37.7, 35.9, 34.8, 33.9, 33.5, 32.1, 26.9 and 26.1 ppm.

Following the general method of Example 1 and using the appropriately substituted aniline, the compounds of Examples 108 to 111 were prepared.

EXAMPLE 108

5-Cyclopentyl-1H-indole-2,3-dione

M.p. 138°–140° C.

13C Nmr (CDCl$_3$) 183.8, 160.2, 147.5, 142.7, 137.8, 124.0, 117.9, 112.5, 45.1, 34.4 and 25.3 ppm.

EXAMPLE 109

7-Cyclopentyl-1H-indole-2,3-dione

1H Nmr (CDCl$_3$) 1.5–1.9 (6H, m), 2.1 (2H, m), 3.0 (1H, m), 7.05 (1H, t), 7.45 (2H, m) and 9.0 (1H, br s) ppm.

EXAMPLE 110

5-Cycloheptyl-1H-indole-2,3-dione

1H Nmr (CDCl$_3$) 1.5–1.9 (12H, m), 2.65 (1H, m), 6.85 (1H, d), 7.4 (1H, dd), 7.45 (1H, d) and 8.6 (1H, br s) ppm.

EXAMPLE 111

7-Cycloheptyl-1H-indole-2,3-dione

1H Nmr (CDCl$_3$) 1.5–2.0 (12H, m), 2.65 (1H, m), 7.05 (1H, t), 7.45 (2H, d) and 8.6 (1H, br s) ppm.

Following the general method of Example 3 and using the appropriately substituted 1H-indole-2,3-dione, the compounds of Examples 112 to 114 were prepared.

EXAMPLE 112

5-Cyclopentyl-1,3-dihydro-2H-indol-2-one

1H Nmr (CDCl$_3$) 1.5–1.9 (6H, m), 2.05 (2H, m), 2.95 (1H, m), 3.55 (2H, s), 6.8 (1H, d), 7.1 (2H, m) and 8.6 (1H, br s) ppm.

EXAMPLE 113

5-Cycloheptyl-1,3-dihydro-2H-indol-2-one

1H Nmr (CDCl$_3$) 1.5–2.0 (12H, m), 2.65 (1H, m), 3.55 (2H, s), 6.8 (1H, d), 7.05 (2H, m) and 8.0 (1H, br s) ppm.

EXAMPLE 114

7-Cycloheptyl-1,3-dihydro-2H-indol-2-one

1H Nmr (CDCl$_3$) 1.5–2.0 (12H, m), 2.65 (1H, m), 3.55 (2H, s), 6.95–7.1 (3H, m) and 8.4 (1H, br s) ppm.

EXAMPLE 115

1,3-Dihydro-5-(1-pyrrolidinyl)-2H-indol-2-one

2-Methyl-4-(1-pyrrolidinyl)-aniline was converted into the N-(tert-butoxycarbonyl) derivative and thence into the title compound using the methodology of R. D. Clark et al, Synthesis 1991, 871–878.

13C Nmr (d$_6$-DMSO) 175.7, 143.8, 133.1, 126.7, 110.0, 109.4, 109.1, 47.8, 36.2 and 24.7 ppm.

EXAMPLE 116

1,3-Dihydro-5-(1-piperidinyl)-2H-indol-2-one

The title compound was prepared from 2-methyl-4-(1-piperidinyl)-aniline using the method of Example 115.

M.p. 154°–156° C.

$^{13}$C Nmr (CDCl$_3$) 177.8, 148.3, 136.2, 126.2, 117.0, 115.4, 109.9, 52.6, 36.7, 25.8 and 24.0 ppm.

EXAMPLE 117

5-Diethylamino-1,3-dihydro-2H-indol-2-one

The title compound was prepared from 4-diethylamino-2-methylaniline using the method of Example 115.

M.p. 122°–124° C.

$^1$H Nmr (CDCl$_3$) 1.1 (6H, t), 3.25 (4H, q), 3.55 (2H, s), 6.6 (1H, dd), 6.75 (2H, m) and 9.0 (1H, br s) ppm.

We claim:

1. A pharmaceutical preparation comprising 5-cyclohexyl-1,3-dihydro-1-[2-[4-(phenylmethyl)-1-piperazinyl]ethyl]-2H-indol-2-one and a pharmaceutically acceptable carrier.

* * * * *